United States Patent

Findeisen et al.

[11] 4,088,665
[45] May 9, 1978

[54] PROCESS FOR THE PARTIAL CARBODIIMIDIZATION OF ORGANIC ISOCYANATES

[75] Inventors: Kurt Findeisen, Odenthal; Kuno Wagner, Leverkusen; Walter Schäfer, Cologne; Hans Joachim Hennig, Leverkusen, all of Germany

[73] Assignee: Bayer Aktiengesellschaft, Leverkusen, Germany

[21] Appl. No.: 715,092

[22] Filed: Aug. 17, 1976

[30] Foreign Application Priority Data

Aug. 23, 1975 Germany .................. 2537685

[51] Int. Cl.$^2$ .................. C07C 119/055; C08G 18/14; C08G 18/78
[52] U.S. Cl. .................. 260/453 AM; 560/26; 560/158; 560/115; 260/25 AT; 260/2.5 AW; 260/2.5 BF; 260/75 NT; 260/77.5 AB; 260/77.5 AT; 260/239 A; 260/389; 260/397.7 R; 260/453 A; 260/453 AB; 260/453 AR; 260/453 AL; 260/453 SP; 260/566 R; 252/182; 544/209
[58] Field of Search ....... 260/453 P, 453 AR, 2.5 BF, 260/453 AL, 453 A, 453 AM, 77.5 AT

[56] References Cited

U.S. PATENT DOCUMENTS

| | | | |
|---|---|---|---|
| 2,853,473 | 9/1958 | Campbell et al. | 260/453 AR |
| 3,931,059 | 1/1976 | LaSpina et al. | 260/2.5 BF |
| 3,941,726 | 3/1976 | Wiedermann et al. | 260/2.5 BF |
| 4,014,935 | 3/1977 | Ibbotson | 260/566 R |

*Primary Examiner*—Dolph H. Torrence
*Attorney, Agent, or Firm*—Gene Harsh; Joseph C. Gil; R. Brent Olson

[57] ABSTRACT

The present invention relates to a new process for the partial carbodiimidization of the isocyanate groups of organic mono-, or di- and/or polyisocyanates, the mixtures which can be obtained by this process and the use of these mixtures as isocyanate components in the production of polyurethane plastics by the known isocyanate polyaddition process. In general, the process comprises:

(a) mixing organic mono-, di- and/or polyisocyanates with 0.1 to 100 ppm of a phosphorus compound of the general formula

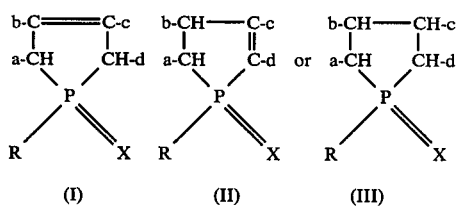

wherein R represents a lower alkyl radical, a phenyl radical, an alkoxy radical, a hydrogen atom or an alkenyl radical; $a$, $b$, $c$ and $d$ each represent hydrogen, a halogen atom, a lower alkyl, lower alkenyl, phenyl, a cyclohexyl or a polymethylene group which together with two neighboring C-atoms of the heterocyclic ring forms a cycloaliphatic ring; and X represents an oxygen or sulphur atom; at a temperature from about 0° to about 200° C, and, (b) terminating the carbodiimidization reaction after the evolution of 1 to 90% of the quantity of carbon dioxide to be theoretically expected in the carbodiimidization of all isocyanate groups present, by the addition of a quantity at least equivalent to the phosphorus compound used of a compound which deactivates the catalysts while forming an adduct therewith.

6 Claims, No Drawings

PROCESS FOR THE PARTIAL CARBODIIMIDIZATION OF ORGANIC ISOCYANATES

BACKGROUND OF THE INVENTION

Carbodiimides can be produced from isocyanates in a particularly simple manner, even at room temperature, by the process which forms the basis of German Auslegeschrift No. 1,130,594 and U.S. Pat. Nos. 2,853,473 and 2,941,966. As disclosed therein, the most important and effective catalysts from the technical point of view, which very quickly carbodiimidize practically any aromatic mono- or polyisocyanate even at room temperature, and which convert unreactive aliphatic or cycloaliphatic mono- or poly-isocyanates into carbodiimides at temperatures above approximately 150° C, are, for example, those corresponding to the formulae:

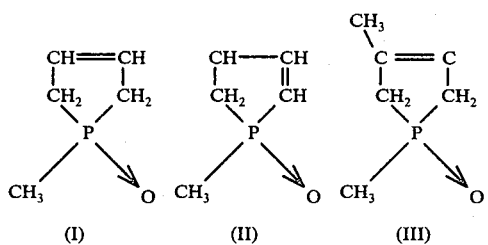

Such catalysts have already found technical application in the production of polycarbodiimide foams.

Unfortunately, hitherto it has not been possible to stop the carbodiimide formation when using the extremely soluble catalysts mentioned above. Consequently, it is difficult to obtain storage stable carbodiimides or poly-carbodiimides containing isocyanate groups. Moreover, it has not been possible with these catalysts to produce stable solutions of diisocyanato carbodiimides, such as

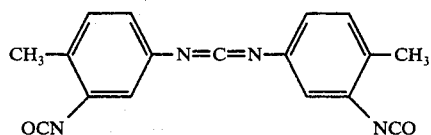

in excess monomeric mono-, di-, or polyisocyanate.

The idea of deactivating the phospholine oxides which are highly effective as catalysts for the carbodiimidization reaction, by the addition of compounds which tend to form salts or adducts with the phospholine oxides, while promising in theory seemed fruitless, since it was known from German Offenlegungsschrift No. 2,245,634, that such adducts themselves constitute carbodiimidization catalysts for isocyanates. In fact, it is recommended in German Offenlegungsschrift No. 2,245,634 that such adducts or salt like compounds be used as catalyst in the production of foams having carbodiimide groups.

DESCRIPTION OF THE INVENTION

It has now been surprisingly found that it is possible to subject mono-, di- and/or polyisocyanates to a partial carbodiimidization reaction to form storage stable isocyanate groups and carbodiimide groups or mixtures having uretoneimine groups formed from these groups by reversible addition, when the phospholine oxide or phospholine sulphide catalysts described below are used in quantities of from 0.1 to 100 ppm, based on the isocyanate or polyisocyanate which is to be partially carbodiimidized, and when deactivation takes place using the deactivating agents described below.

The object of the present invention is therefore a process for the partial carbodiimidization of the isocyanate groups of mono-, di-, and/or polyisocyanates, comprising (a) mixing organic mono-, di- and/or polyisocyanates with 0.1 to 100 ppm of a phosphorus compound of the general formula:

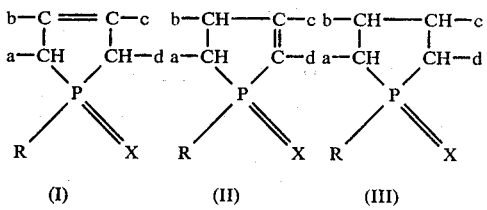

wherein R represents a lower alkyl radical, a phenyl radical, an alkoxy radical, a hydrogen atoms or an alkenyl radical; a, b, c and d each represent hydrogen, a halogen atom, a lower alkyl, lower alkenyl, phenyl, a cyclohexyl or a polymethylene group which together with two neighboring C-atoms of the heterocyclic ring forms a cycloaliphatic ring; and X represents an oxygen or sulphur atom; at a temperature from about 0° to about 200° C, and, (b) terminating the carbodiimidization reaction after the evolution of 1 to 90% of the quantity of carbon dioxide to be theoretically expected in the carbodiimidization of all isocyanate groups present, by the addition of a quantity at least equivalent to the phosphorous compound used of a compound which deactivates the catalysts while forming an adduct therewith.

The invention also relates to the storage stable mixtures having isocyanate and carbodiimide groups which can be obtained by this process, characterized by a content of 0.1 to 100 ppm of phosphorus compounds of the formulae:

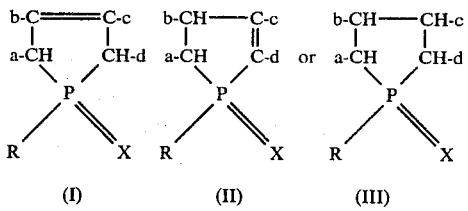

in their deactivated form in respect to their catalytic effect by adduct formation with compounds of the formula R'Y, wherein R represents an unsubstituted alkyl radical having from 1 to 4 carbon atoms, an unsubstituted alkoxy radical having from 1 to 4 carbon atoms or a phenyl radical; a, b, c, d which are identical or different and represent hydrogen or an unsubstituted alkyl radical having from 1 to 4 carbon atoms, and X represents oxygen, and wherein R' represents hydrogen or a radical by the removal of a halogen atom of an acid halide group from an inorganic or organic acid halide, and Y represents chlorine or bromine.

The present invention also relates to the use of these isocyanate mixtures as isocyanate components in the production of polyurethane plastics by the known isocyanate-polyaddition reaction, e.g., the reaction of an organic isocyanate with an active-hydrogen containing material.

In the process according to the invention, the isocyanate to be partially carbodiimidized is mixed with the carbodiimidization catalyst at temperatures of from about 0° to about 200° C, and (in the case of aromatic isocyanates) preferably at 50° to 150° C, and most preferably at 90° to 110° C, the carbodiimidization reaction is conducted to the desired degree of carbodiimidization within the specified temperature ranges and upon reaching the desired degree of carbodiimidization the reaction is terminated by the addition of a deactivator in an amount which is at least equivalent to the catalyst.

"The degree of carbodiimidization" is herein defined as the percentage of isocyanate groups present in the starting isocyanate which are converted into carbodiimide groups with the evolution of carbon dioxide by the process according to the invention. The degree of carbodiimidization can be determined during the process according to the invention by the quantity of carbon dioxide evolving from the reaction mixture. This volumetrically determinable carbon dioxide quantity thus provides information on the degree of carbodiimidization achieved at any time during the process of the invention. In the process of the invention the carbodiimidization reaction is terminated on reaching a degree of carbodiimidization of from 1 to 90%, and preferably from 5 to 30%.

Carbodiimidization catalysts which are suitable for the process according to the invention are organic phosphorous compounds of the above formulae (I), (II) and (III). These phosphorous compounds are known and can be produced by known processes (cf. G. M. Kosolapoff, L. Maier, Organic Phosphorous Compounds, Wiley-Interscience, New York, 1972 et seq. Vol 3, pages 370 to 371, pages 458 to 463 and Vol. 4, pages 9 to 10, page 48). Such phospholine oxides and sulphides or phospholidine oxides or sulphides are described in U.S. Pat. Nos. 2,663,737, 2,663,738, 2,663,739, 2,941,966 and 2,853,473, the disclosures of which are herein incorporated by reference. In the process according to the invention it is preferable to use phospholine oxides or sulphides. Specific examples of useful materials include 1-methyl-1-oxophospholine, 1-ethyl-1-oxophospholine, 1-butyl-1-oxophospholine, 1-(2-ethylhexyl)-1-oxophospholine, 1-methyl-1-thiophospholine, 1-(2-chloroethyl)-1-oxophospholine, 1-phenyl-1-oxophospholine, 1-p-tolyl-1-oxophospholine, 1-chloromethyl-1-oxophospholine, 1,3-dimethyl-1-oxophospholine, 1,2-dimethyl-1-oxophospholine, 1-methyl-3-chloro-1-oxophospholine, 1-methyl-3-bromo-1-oxophospholine, 1-chlorophenyl-1-oxophospholine, 1,3,4-trimethyl-1-oxophospholine, 1,2,4-trimethyl-1-oxophospholine, 1,2,2-trimethyl-1-oxophospholine, 1-phenyl-1-thiophospholine, 1-phenyl-3-methyl-1-oxophospholine and 1-phenyl-2,3-dimethyl-1-oxophospholine.

These compounds generally have a double bond either in the 2,3 or in the 3,4 position. In general in the process according to the invention, phospholine oxides or sulphides are used which are technical mixtures both of the 2,3 and the 3,4 I unsaturated compounds.

Catalysts which are particularly preferred for use in the process according to the invention are those of the above specified formulae (I) and (II), in which R represents an unsubstituted alkyl radical having from 1 to 4 carbon atoms, an unsubstituted alkoxy radical having from 1 to 4 carbon atoms or a phenyl radical; $a$, $b$, $c$ and $d$ which are identical or different radicals represent hydrogen or an unsubstituted alkyl radical having from 1 to 4 carbon atoms, and X represents oxygen.

The process according to the invention can also be carried out with the phospholidine oxides corresponding to the above formulae (III). The corresponding phospholines are also suitable in principle but less preferred.

Compounds used as deactivating agents are those which react with the catalyst to form salts or adducts. Preferred compounds of this type are those of the formula R'Y, in which R' represents hydrogen or a radical obtained by the removal of a halogen atom from an acid halide group of an inorganic or organic acid halide, and Y represents a halogen atom, preferably chlorine or bromine.

Examples of such preferred deactivating agents to be used in the process of the invention include hydrogen chloride, hydrogen bromide, thionyl chloride, thionyl bromide, sulphuryl chloride, sulphuryl bromide, phosphoroxy chloride, phosphoroxide bromide, acetyl chloride, acetyl bromide, benzoyl chloride, oxalyl chloride, or carbamic acid chlorides and bromides of the isocyanates disclosed below.

In addition to these deactivators (the use of which is preferred in the process of the invention), other compounds with labile chloride or bromide bonds can be used, the only requirement being that they react with the catalysts of the invention to form salts (e.g., by the formation of a 4 bond, positively charged phosphorus atom and a chloride or bromide anion). Such compounds which are suitable for the process according to the invention but are not technically "acid chlorides" include, for example, phosphorus trichloride, phosphorous tribromide, phosphorus pentachloride, phosphorous, pentabromide, silicon tetrachloride, antinomy pentachloride, trichloromethylsilane and the like.

In addition to these compounds, inorganic halides can also be used as deactivators, which halides react with the catalysts according to the invention to form adducts. These include, in particular, metal-II-chlorides, metal-II-bromides, metal-III-chlorides or metal-III-bromides of metals of the second and third main and subsidiary groups and of the eighth subsidiary group of the Periodic Table of Elements. Specific examples of such compounds include calcium chloride, zinc chloride, aluminium chloride, iron-II-chloride, iron-III-chloride and the corresponding bromides. Compounds such as borontrifluoride or borontrichloride, which are capable of adduct formation with the catalysts of the instant invention, are also usable but are generally less desirable.

The deactivators are generally used in the process of the invention in quantities which are at least equivalent to the quantity of the catalyst used. In other words at least 1 mol, and preferably from 1 to 3 mols, of deactivator are used per mol of catalyst.

In principle, in the process according to the invention, any aliphatic, cycloaliphatic, araliphatic aromatic and hetrocyclic di and/or polyisocyanates can be carbodiimidized. These isocyanates are known and are described, for example, by W. Siefken in Justus Liebigs Annalen der Chemie, 562 pages 75 to 136. Specific examples include ethylene diisocyanate; 1,4-tetramethylenediisocyanate; 1,6-hexamethylene-diisocyanate;

1,12-dodecanediisocyanate; cyclobutane-1,3-diisocyanate; cyclohexane-1,3- and 1,4-diisocyanate and any mixtures of these isomers; 1-isocyanato-3,3,5-trimethyl-5-isocyanatomethyl-cyclohexane (German Auslegeschrift No. 1,202,785, U.S. Pat. No. 3,401,190); 2,4-and 2,6-hexahydrotolylenediisocyanate and any mixtures of these isomers; hexahydro-1,3- and/or -1,4-phenylenediioscyanate; perhydro-2,4'- and/or -4,4'-diphenylmethanediisocyanate; 1,3- and 1,4-phenylenediisocyanate; 2,4- and 2,6-tolylenediisocyanate and any mixtures of these isomers; diphenylmethane-2,4'- and/or -4,4'-diisocyanate; naphthylene-1,5-diisocyanate; triphenylmethane-4,4',4'''-triisocyanate; polyphenyl-polymethylene-polyisocyanate such as obtained by aniline formaldehyde condensation and subsequent phosgenation and described in British Pat. Nos. 874,430 and 848,671; m- and p-isocyanato phenyl-sulphonylisocyanates according to U.S. Pat. No. 3,454,606; perchlorinated arylpolyisocyanates, as described in U.S. Pat. No. 3,277,138; polyisocyanates having carbodiimide groups, as described in U.S. Pat. No. 3,152,162; diisocyanates as described in U.S. Pat. No. 3,492,330; polyisocyanates having allophanate groups, as described for example in British Pat. No. 994,890, Belgian Pat. No. 761,626 and published Dutch Patent application No. 7,102,524; polyisocyanates having isocyanurate groups, as for example, described in U.S. Pat. No. 3,001,973, in German Pat. Nos. 1,002,789, 1,222,067 and 1,027,394 and in German Offenlegungsschriften Nos. 1,929,034 and 2,004,048; polyisocyanates having urethane groups, as, for example, described in Belgian Pat. No. 752,261 or in U.S. Pat. No. 3,394,164; polyisocyanates having acylated urea groups according to German Pat. No. 1,230,778; polyisocyanates having biuret groups, as described for example in U.S. Pat. Nos. 3,124,605 and 3,201,372 and in British Pat. No. 889,050; polyisocyanates produced by telomerization reactions, as described, for example, in U.S. Pat. No. 3,654,106; polyisocyanates having ester groups, as for example, described in British Pat. Nos. 965,474 and 1,072,956, in U.S. Pat. No. 3,567,763 and in German Pat. No. 1,231,688; reaction products of the above mentioned isocyanates with acetals according to German Pat. No. 1,072,385; and polyisocyanates containing polymeric fatty acid radicals according to U.S. Pat. No. 3,455,883. It is also possible to use the distillation residues containing isocyanate groups, which occur in commercial isocyanate production, optionally dissolved in one or more of the above-mentioned polyisocyanates. In addition, it is possible to use mixtures of any of the above mentioned polyisocyanates.

Preferred isocyanates for use in the process according to the invention are aromatic polyisocyanates such as 2,4-diisocyanatotoluene, 2,6-diisocyanatotoluene, 4,4'-diisocyanatodiphenylmethane, polyisocyanate mixtures of the diphenylmethane series obtained by phosgenation of aniline/formaldehyde condensates, m-phenylenediisocyanate, p-phenylenediisocyanate and any mixtures of these polyisocyanates.

In principle, it is also possible to partially carbodiimidize mono-isocyanates in the process according to the invention or to use them in the mixture with known polyisocyanates. Suitable mono-isocyanates include for example, methylisocyanate, ethylisocyanate, propylisocyanate, isopropylisocyanate, n-butylisocyanate, n-hexylisocyanate, ω-chlorophenylisocyanate, phenylisocyanate, tolylisocyanate, p-chlorophenylisocyanate, 2,4-dichlorophenylisocyanate and trifluoromethylphenylisocyanate.

The process according to the invention can be performed in the presence or in the absence of solvents which are inert towards the polyisocyanates or auxiliary and additional substances. Suitable solvents are, for example, toluene, xylene, chlorobenzene, o-dichlorobenzene, decalin, dimethylformamide, dimethylacetamide, butylacetate, carbontetrachloride, trichloroethylene and tetramethylurea.

To carry out the process according to the invention, 0.1 to 100 ppm, and preferably from 1 to 60 ppm of the catalyst based on the isocyanate is introduced with stirring at a temperature of from 0° to 200° C, preferably 50° to 150° C, and most preferably 90° to 110° C, optionally under pressure, into the liquid or dissolved isocyanate. After reaching the desired degree of carbodiimidization, the reaction is terminated by the addition of the deactivating agent. Yet another variation of the process is to synthesize the salt or the adduct from the catalyst (cf. German Offenlegungsschrift No. 2,245,634) and deactivating agent and to mix the mono- or preferably di- or polyisocyanates with 0.2 to 200 ppm, and preferably 2 to 120 ppm of the adduct; and by the addition of a base to release 0.1 to 100 ppm, (preferably 1 to 60 ppm), of the phosphorus compounds and to then carbodiimidize to the desired degree of carbodiimidization and to stop the carbodiimidization by the addition of at least the stoichiometric quantity of the deactivating agent based on the catalyst. On adding the catalytically active phosphorous compound to the mono- or preferably di- and/or polyisocyanates used according to the invention, it is seen that more or less of the catalytically active phosphorus compounds must be used to achieve carbodiimidization as a function of their halogen content, because a deactivation of the catalyst occurs.

The catalyst quantity can be further reduced by the addition of at least the stoichiometric quantity of a base relative to the halogen content of the mono- or, preferably, di- or polyisocyanates, since a premature deactivation of the catalyst does not take place under these conditions.

A particular advantage of the process according to the invention is the fact that it permits the production of only partially carbodiimidized mono-, di- and/or polyisocyanates in a particularly simple manner, the substances being distinguished by a particularly low content of foreign substance (deactivated catalyst). The mixtures so produced also have the advantage that the deactivated catalysts present in them can be reactivated by the simple addition of a base. This provides the possibility of renewed carbodiimidization to a specific higher degree of carbodiimidization. The renewed addition of a deactivating agent then again leads to storage stable mixtures. In principle, it is also possible to insert a NCO-polyaddition reaction between these two stages of the carbodiimidization reaction to produce prepolymers having NCO groups, which can then be further carbodiimidized by reactivating the catalyst.

The carbodiimides having isocyanate groups according to the invention or their solutions in carbodiimide-free polyisocyanates are valuable starting products for the diisocyanates-polyaddition process and can be used for the production of plastics varying from hard to elastic, optionally in cellular form, for the production of varnishes, coverings, coatings, films and molded bodies. Polyurethanes produced in this way contain in the polymer molecule permanently incorporated carbodiimide groups or uretoneimine groups (=masked carbodiimide groups), which at the same time constitute anti-ageing agents against the hydrolysis of ester compounds and also reduce the inflammability of the plastics.

The production of polyurethanes from the polyisocyanate mixtures according to the invention takes place in known manner by reaction with high and optionally also low molecular weight compounds, having at least 2 hydrogen atoms capable of reacting with isocyanates.

These active hydrogen materials include compounds having amino groups, thiol groups, or carboxyl groups and preferably hydroxyl groups. Particularly preferred are compounds having 2 to 8 hydroxyl groups, particularly those of a molecular weight of from 400 to 10,000, preferably 800 to 6,000, such as polyesters, polyethers, polythioethers, polyacetals, polycarbonates and polyesteramides. These materials have at least 2, and usually from 2 to 8, but preferably 2 to 4 hydroxyl groups, and are known for the production of homogeneous and cellular polyurethanes.

The polyesters having hydroxyl groups include, for example, reaction products of polyhydric, (preferably, dihydric and optionally trihydric alcohols) with polybasic, (preferably dibasic), carboxylic acids. Instead of the free carboxylic acids, the corresponding polycarboxylic acid anhydrides or corresponding polycarboxylic acid esters of lower alcohols or mixtures thereof can be used for the production of the polyesters. The polycarboxylic acids may be aliphatic, cycloaliphatic, aromatic and/or heterocyclic and optionally may be substituted e.g. by halogen atoms, and/or unsaturated. Useful acidic materials include succinic acid, adipic acid, suberic acid, azelaic acid, sebacic acid, phthalic acid, isophthalic acid, trimellitic acid, phthalic acid, anhydride, tetrahydrophthalic acid anhydride, hexahydrophthalic acid anhydride, tetrachlorophthalic acid anhydride, endomethylenetetrahydrophthalic acid anhydride, glutaric acid anhydride, maleic acid, maleic acid anhydride, fumaric acid, dimeric and trimeric fatty acids such as oleic acid, optionally in admixture with monomeric fatty acids, terephthalicaciddimethylester and terephthalic acid-bis-glycol ester. Useful polyhydric alcohols include ethyleneglycol, propyleneglycol-(1,2) and-(1,3), butyleneglycol-(1,4) and -(2,3), hexanediol-(1,6), octanediol-(1,8), neopentylglycol, cyclohexanedimethanol (1,4-bis-hydroxymethylcyclohexane), 2-methyl-1,3-propanediol, glycerine, trimethylolpropane, hexanetriol-(1,2,6) butanetriol-(1,2,4), trimethylolethane, pentaerythritol, quinite, mannitol, sorbitol, methylglycoside, diethyleneglycol, triethyleneglycol, tetraethyleneglycol, polyethyleneglycols, dipropyleneglycol, polypropyleneglycols, dibutyleneglycol and polybutyleneglycols. The polyesters may have a proportion of end carboxyl groups. Polyesters of lactones, e.g. ε-caprolactone, or hydroxycarboxylic acids, e.g. ω-hydrocaproic acids, can also be used.

The polyethers useful herein are of the known type and are produced, for example, by polymerization of epoxides, such as ethylene oxide, propylene oxide, butylene oxide, tetrahydrofuran, styrene oxide or epichlorohydrin with themselves, e.g. in the presence of $BF_3$, or by the addition of these epoxides, optionally in admixture with each other to starting components having reactive hydrogen atoms such as water, alcohols or amines. Examples of alcohols and amines include ethylene-glycol, propyleneglycol-(1,3) or -(1,2),trimethylolpropane, 4,4'-dihydroxyphenylpropane, aniline, ammonia, ethanolamine, and ethylenediamine. Sucrose polyethers as for instance described in German Auslegeschriften Nos. 1,176,358 and 1,064,938 can also be used. The polyethers which are greatly preferred are those which have predominant amounts of primary OH-groups (up to 90% by weight relative to all OH-groups present in the polyether). Polyethers modified by vinyl polymers, as for example those produced by the polymerization of styrene and acrylonitrile in the presence of polyethers (U.S. Pat. Nos. 3,383,351, 3,304,273, 3,523,093, 3,110,695; German Pat. No. 1,152,536), are suitable, as are polybutadienes having OH-groups.

The condensation products of thiodiglycol with itself and/or with other glycols, dicarboxylic acids, formaldehydes, amino carboxylic acids or amino alcohols can also be used herein. Depending on the co-components, these products are polythio mixed ethers, polythioether esters, or polythioether ester amides.

The polyacetals which can be produced from glycols, such as diethyleneglycol, triethyleneglycol, 4,4'-dioxethoxydiphenyldimethylmethane, and hexandiol, and formaldehyde can also be used. Polyacetals suitable for use according to the invention can also be produced by the polymerization of cyclic acetals.

The known type of polycarbonates having hydroxyl groups are also useable and include those which can be produced, for example, by the reaction of diols, such as propanediol-(1,3), butanediol-(1,4), and/or hexanediol-(1,6), diethyleneglycol, triethyleneglycol or tetraethyleneglycol, with diaryl carbonates, e.g. diphenyl carbonates, or phosgene.

The polyester amides and polyamides include, for example, the predominantly linear condensates obtained from polyvalent saturated and unsaturated carboxylic acids or their anhydrides and polyhydric saturated and unsaturated amino alcohols, diamines, polyamines and mixtures thereof.

Polyhydroxyl compounds already containing urethane- or urea groups and, optionally, modified natural polyols, such as castor oil, carbohydrates or starch, can also be used. The addition products of alkylene oxides to phenol-formaldehyde-resins or to urea-formaldehyde-resins can also be used according to the invention.

Examples of the many active hydrogen containing compounds useable in the instant invention are described in, for example, High Polymers, Vol. XVI, "Polyurethanes, Chemistry and Technology", by Saunders-Frisch, Interscience Publishers, New York, London, Vol I, 1962, pages 32 to 42 and pages 44 to 54 and Vol II, 1964, pages 5 to 6 and 198 to 199, and in the Kunststoff-Handbuch, Vol; VII, Vieweg-Höchtlen, Carl-Hanser-Verlag, München 1966, on pages 45 to 71.

Of course, mixtures of the above-mentioned active hydrogen containing compounds with at least 2 hydrogen atoms which are reactive towards isocyanates, having a molecular weight of 400 to 10,000 (e.g. mixtures of polyethers and polyesters), can also be used. Compounds having at least 2 hydrogen atoms reactive towards isocyanates and having molecular weights of 32 to 400 can also be used as starting components. Such compounds include compounds having hydroxyl groups and/or amino groups and/or thiol groups and/or carboxyl groups, and preferably compounds having hydroxyl groups and/or amino groups, which serve as chain extending agents or cross linking agents. These compounds generally have 2 to 8 hydrogen atoms which are reactive towards isocyanates, and preferably contain 2 or 3 reactive hydrogen atoms. Examples of such compounds include: ethyleneglycol, propyleneglycol-(1,2) and -(1,3), butyleneglycol-(1,4) and -(2,3), pentandiol-(1,5), hexanediol-(1,6), octandiol-(1,8), neopentylglycol, 1,4-bis-hydroxymethylcyclohexane, 2-methyl-1,3-propanediol, glycerine, trimethylolpropane, hexanetriol-(1,2,6), trimethylolethane, pentaerythrite, quinitol, mannitol and sorbitol, diethyleneglycol, triethyleneglycol, tetraethyleneglycol, polyethyleneglycol having a molecular weight of up to 400, dipropyleneglycol, polypropyleneglycols with a molecular weight of up to 400, dibutyleneglycol, polybutyleneglycols having a molecular weight of up to 400, 4,4'-dihydroxydiphenylpropane, di-hydroxymethylhydroquinone, ethanolamine, diethanolamine, trimethanolamine, 3-aminopropanol, ethylenediamine, 1,3-diaminopropane, 1-mercapto-3-aminopropane, 4-hydroxy- or -amino-phthalic acid, succinic acid, adipic acid hydrazine, N,N'-dimethylhydrazine and 4,4'-diaminodiphenylmethane. Mixtures of different compounds having at least 2 hydrogen atoms reactive towards isocyanates and having a molecular weight of from 32 to 400 can also be used.

Water and/or volatile organic substances are used as blowing agents in the production of foams according to the invention. Such blowing agents include, for example, acetone, ethylacetate, halogen substituted alkanes such as methylenechloride, chloroform, ethylidenechloride, vinylidenechloride, monofluorotrichloromethane, chlorodifluoromethane, dichlorodifluoromethane, and in addition butane, hexane, heptane, or diethylether. A blowing effect can also be achieved by the addition of compounds which decompose at temperatures above room temperature to evolve gases, for example, nitrogen, e.g. azo compounds such as azoisobutyricacidnitrile. Further examples of blowing agents and details concerning the use of blowing agents are described in the Kunststoff-Handbuch, Volume VII, edited by Vieweg and Höchtlen, Carl-Hanser-Verlag, Munchen 1966, pages 108 and 109, 453 to 455 and 507 to 510.

In addition, catalysts are often used in the isocyanate addition process according to the invention. These catalysts are generally known and include tertiary amines, such as triethyl amine, tributylamine, N-methyl-morpholine, N-ethyl-morpholine, N,N,N',N'-tetramethylethylenediamine, 1,4-diaza-bicyclo-(2,2,2)-octane, N-methyl-N'-dimethyl-aminoethylpiperazine, N,N-dimethylbenzylamine, bis-(N,N-diethylaminoethyl)-adipate, N,N-diethylbenzylamine, pentamethyldiethylenetriamine, N,N-diemthylcyclohexylamine, N,N,N',N'-tetramethyl-1,3-butanediamine, N,N-dimethyl-$\beta$-phenylethyl-amine, 1,2-dimethylimidazol, 2-methylimidazol. Known Mannich bases produced from secondary amines, such as dimethylamine, and aldehydes, preferably formaldehydes, or ketones such as acetone, methylethylketone and cyclohexanone, and phenols, such as phenol, nonylphenol and bis-phenol can also be used as catalysts.

Tertiary amines having hydrogen atoms which are active in relation to isocyanate groups can also be used as catalysts and include for example, triethanolamine, triisopropanolamine, N-methyl-diethanolamine, N-ethyldiethanolamine, N,N-dimethyl-ethanolamine, and their reaction products with alkylene oxides, such as propylene oxide and/or ethylene oxide.

Also suitable are silamines with carbon-silicon bonds, such as described, for example in U.S. Pat. No. 3,620,984. Examples include e.g., 2,2,4-trimethyl-2-silamorpholine and 1,3-diethylaminomethyl-tetramethyl-disiloxane.

Also suitable are nitrogen-containing bases such as tetraalkylammonium-hydroxides, and alkali hydroxides such as sodium hydroxide, alkali phenolates such as sodium phenolate or alkali alcoholates such as sodium methylate. Hexahydrotriazines can also be used as catalysts.

According to the invention, organometallic compounds, and in particular organotin compounds, can also be used as catalysts.

Organotin compounds which can be used include tin(II)-salts of carboxylic acids such as tin(II)-acetate, tin(II)-octoate, tin(II)-ethylhexoate and tin(II)-laurate and the tin(IV)-compounds e.g. dibtuyltinoxide, dibutyltindichloride, dibutyltindiacetate, dibutyltindilaurate, dibutyltinmaleate or dioctiletindiacetate. Of course mixtures of all the above mentioned catalysts can be used.

Further examples of catalysts to be used according to the invention and details concerning the use of the catalysts are described in the Kunststoff-Handbuch, Volume VII, edited by Vieweg and Höchtlen, Carl-Hanser-Verlag, Munich 1966, on pages 96 to 102.

The catalysts, when used, are generally used in a quantity between 0.001 and 10% by weight, based on the quantity of compounds with at least 2 hydrogen atoms which are reactive towards isocyanates, having molecular weights of 400 to 10,000.

According to the invention, surface active additives, such as emulsifiers and foam stabilizers, can also be used. Emulsifiers which can be used include for example the sodium salts, castor oil sulphonates, or salts of fatty acids with amines, such as diethylamine, with oleic acid or diethanolamine with stearic acid. Alkali- or ammonium salts of sulphonic acids (such as dodecylbenzene sulphonic acid or dinaphthylmethane disulphonic acid) or fatty acids (such as ricinoleic acid) or polymeric fatty acids, can also be used as surface active additives.

Foam stabilizers which can be used include, polyethersiloxanes, and in particular water soluble examples thereof. These compounds are generally structured in such a way that a copolymer of ethylene oxide and propylene oxide is associated with a polydimethylsiloxane radical. Such foam stabilizers are, for example, described in U.S. Pat. Nos. 2,834,748, 2,917,480 and 3,629,308.

Reaction retarders can also be used according to the invention (e.g. acid reacting substances such as hydrochloric acid or organic acid halides). Cell regulators of known type (such as paraffins or fatty alcohols or dimethylpolysiloxanes) pigments, dyes, flame proofing agents of known type, (e.g. tris-chloroethylphosphate, tricresylphosphate or ammonium phosphate and polyphosphate), stabilizers against the effects of ageing and weathering, softeners having a fungistatic and bacteriostatic effect, and fillers (such as barium sulphate, kieselguhr, carbon black or prepared chalk), can also be used if desired.

Further examples of surface active additive foam stabilizers, cell regulators, reaction retarders, stabilizers, flame retarding substances, softeners, dyes and fillers and substances having a fungistatic and bacteriostatic effect and details concerning the manner of use and effects of these additives are described in the Kunststoff-Handbuch, Volume VII, edited by Vieweg and Höchtlen, Carl-Hanser-Verlag, Munich 1966, pages 103 to 113.

According to the invention the reactants for the isocyanate-addition process are brought together by the known one stage process, the prepolymer process or the semi-prepolymer process. Mechanized devices are often used, e.g. those which are described in U.S. reissue Patent 24,514. Details concerning processing devices which can also be used in the invention are described in the Kunststoff-Handbuch, Volume VII, edited by Vieweg and Höchtlen, Carl-Hanser-Verlag, Munich 1966 on pages 121 to 205.

In cellular plastic production foaming is often conducted in molds. The mold material can be metal, e.g. aluminum, or plastic, e.g. epoxy resin. The reaction mixture foams in the mold and forms the molding. The in-mold foaming can be performed in such a way that the molding has a cellular structure on its surface, but it can also be performed in such a way that the molding has a compact skin and a cellular core. In this connection, it is possible to proceed in such a way that sufficient foamable reaction mixture is placed into the mold, so that the cellular plastic formed fills the mold. However, it is also possible to work in such a way that more foamable reaction mixture is placed in the mold than is necessary to fill the interior of the mold with cellular plastic. In the latter case work is carried out by "overcharging"; such a procedure is for example known from U.S. Pat. Nos. 1,178,490 and 3,182,104.

In in-mold forming, known "external mold release agents" such as silicon oils are often used. So-called "internal mold release agents" can also be used, optionally in a mixture with external release agents as for example described in German Offenlegungsschriften Nos. 2,121,670 and 2,307,589. Strain hardenable cellular plastics can also be produced using the materials of the instant invention (cf. British Pat. No. 1,162,517 and German Offenlegungsschrift No. 2,153,086).

Cellular plastics can also be produced by block foaming or by the known double conveyor belt method.

The following examples serve to illustrate the present invention. Unless otherwise indicated quantities are given in parts by weight or percentage by weight.

EXAMPLES

In all the examples the NCO-content masked by uretonimine formation was determined in the NCO-titration. (Phospholine oxide = 1-methyl-1-oxo-phospholine, technical isomer mixture).

EXAMPLE 1

500 g of 4,4'-diisocyanatodiphenylmethane were heated to 95° C in a 1 liter 3 necked flask and mixed with 0.2 ml of a 3% phospholine oxide solution in toluene. After 45 minutes, 5.2 liters of carbon dioxide was measured with the gas meter. The $CO_2$ evolution was halted by the addition of 0.2 ml of butylcarbamic acid chloride and the mixture was restirred for 30 minutes at 95° C. No further $CO_2$ evolution took place.

489 g of carbodiimidized 4,4'-diisocyanatodiphenylmethane with a NCO-content of 29.6% and a viscosity $\eta_{25°\ C}$ of 39.9 cP was obtained after cooling. The product was storage stable for 6 months.

EXAMPLE 2

1 kg of 4,4'-diisocyanatodiphenylmethane was heated to 100° C and mixed at this temperature with 0.4 ml of a 3% phospholine oxide solution in xylene. 25 liters of $CO_2$ evolved after 1 hour, which was measured with a gas meter. After deactivating the phospholine oxide with 1 g of cyclohexycarbamic acid chloride the mixture was restirred for 30 minutes to check the $CO_2$ evolution. As no more $CO_2$ development took place, the deactivation of the catalyst is terminated.

950 g of partially carbodiimidized 4,4'-diisocyanatodiphenylmethane was obtained having an NCO-content of 22.4% a viscosity $\eta_{25°\ C}$ of 1746 cP. The product was again analytically examined after three weeks and it was ascertained that the NCO-content was 22.3%, and that the viscosity had risen to $\eta_{25°\ C}$: 8480 cP by uretoneimine formation. After three months the NCO-content was 22% and the viscosity $\eta_{25°\ C}$ was 9050 cP. The reaction produce was storage stable.

EXAMPLE 3

1 kg of 4,4'-diisocyanatodiphenylmethane was mixed as described in Example 2 with 0.2 ml of a 3% phospholine oxide solution in toluene and in 90 minutes 30.7 liters of carbon dioxide was measured. Deactivation took place with 1 g of 4,4'-dicarbamoylchloridediphenylmethane. 940 g of partially carbodiimidized 4,4'-diisocyanatodiphenylmethane having an NCO-content of 19.5% and a viscosity $\eta_{25°\ C}$ of 34542 cP was obtained. The reaction product was storage stable.

EXAMPLE 4

The following example shows that mixtures of tolylenediisocyanate-2,4 and tolylene-diisocyanate-2,6, in which the isomer ratio is approximately 80:20, can be carbodiimidized to a desired NCO-content in a smooth and efficiently running reaction.

1 kg of the above mixture was heated to 125 to 130° C and 0.4 ml of a 3% phospholine oxide solution was added at once. A vigorous $CO_2$ evolution occurred and after 70 minutes 51 liters of $CO_2$ was generated. The catalyst was deactivated by the addition of 0.6 ml of thionyl chloride, and the $CO_2$ evolution was interrupted. To ensure that the gas evolution had finished, the mixture was restirred for 30 minutes. 899 g of partially carbodiimidized tolylene-diisocyanate-2,4/-2,6 mixture was obtained. The NCO-content was 30.9% and the viscosity $\eta_{25°\ C}$ was 646 cP. Storage stability was noted for a period of 6 months. Measurements in closed vessels showed that no $CO_2$ overpressure was built up.

EXAMPLE 5

87 g of tolylene diisocyanate were mixed in a 500 ml 3 necked flask with 0.1 ml of a 3% phospholine oxide solution in methanol. The reaction mixture was heated for 30 minutes to 110° C, and 6.7 liters of carbon dioxide were evolved. The carbodiimidization was terminated by the addition of 0.1 ml of phosphoroxy chloride. 242 g of a partially carbodiimidized mixture having an NCO-content of 40.7% and a viscosity $\eta_{25°\ C}$ of 14 cP was obtained.

EXAMPLE 6

87 g of tolylenediisocyanate-2,4 and 125 g of 4,4'-diisocyanatodiphenylmethane were mixed in a 500 ml 4 necked flask provided with stirrer, thermometer gas outlet pipe (or inlet pipe) and dropping funnel with 0.7 ml of a 5% phospholine oxide solution. After 2 hours, 6 liters of $CO_2$ had evolved. By introducing of 50 ppm phosgene, the $CO_2$ evolution was terminated. 200 g of a mixture of partially carbodiimidized tolylenediisocyanate-2,4 and 4,4'-diisocyanatodiphenylmethane with an NCO-content of 28.7% and a viscosity $\eta_{25°\ C}$ of cP was obtained.

EXAMPLE 7

702 g of a biuretized hexamethylenediisocyanate of the following idealized composition:

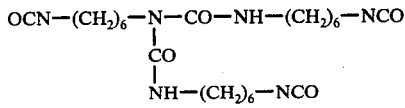

was mixed with 87 g of tolylenediioscyanate-2,4 and heated to 100° C. After the addition of 5 ppm phospholine oxide 10 liters of carbon dioxide had evolved. Further carbodiimidization was stopped by the addition of 15 ppm phosphorous trichloride. A mixture of carbodiimidized tolylene diisocyanate-2,4 and biuretized hexamethylenediisocyanate was obtained.

Yield: 765 g
NCO-content 20.3%
$\eta_{25°C}$ 17,000 cP

EXAMPLE 8

A glass vessel (5 liters) provided with a stirrer, a nitrogen mixture to purge the glass vessel and a $CO_2$ outlet pipe, which was connected to a gas meter, was filled with 2.91 kg of 4,4'diisocyanatodiphenylmethane and heated for 1 hour to 65° C after being purged with $N_2$. The carbodiimidization was initiated by the addition of 1 ml of 3% phospholine oxide solution. Carbon dioxide evolution was stopped after the evolution of 24.4 liters of $CO_2$ by the addition of 0.6 ml sulphurylchloride.

2.86 kg of partially carbodiimidized 4,4'-diisocyanatodiphenylmethane having an NCO-content of 30% and a viscosity $\eta_{25°C}$ of 32 cP was obtained.

EXAMPLE 9

168 g of freshly distilled hexamethylenediioscyanate was heated in a reactor to 160° C and partially carbodiimidized after the addition of 0.8 ml of a 3% phospholine oxide solution in hexamethylenediisocyanate. After 6 liters of $CO_2$ had been evolved, further carbodiimidization was stopped by the introduction of 0,4 g HCl gas.

Yield: 155 g partially carbodiimidized hexamethylenediisocyanate
NCO-content: 32.3%

EXAMPLE 10

222 g of fresh distilled isophoronediisocyanate was heated in a reaction vessel to 150° C and partially carbodimidized after the addition of 1.5 ml of a 3% phospholine oxide solution. The carbodiimidization was terminated after the evolution of 6.3 liters carbon dioxide by the addition of 1 ml silicon tetrachloride.

208 g of partially carbodiimidized isophorenediisocyanate having an NCO-content of 26.8% and a viscosity $\eta_{25°C}$ of 1530 was obtained.

EXAMPLE 11

119 g of phenylisocyanate was mixed with 1 ml of a 3% phospholine oxide solution in toluene and, after the evolution of 3 liters of $CO_2$, further carbodiimidization was terminated by the addition of 1 g phenylcarbamic acid chloride. After sometime, the reaction product begins to crystallize and 110 g of the triphenyluretonimine are obtained.

Melting point: 119° C

NCO-content during hot titration: 13.4%.

EXAMPLE 12

1,000 g of 4,4'-diisocyanatodiphenylmethane having a saponifiable halogen content of 100 ppm was heated to 70° C and mixed with 150 ppm of triethylamine in a 2 liter 4-necked flask with stirrer, 2 dropping funnels and a carbon dioxide outlet pipe. The rapid carbon dioxide development begins after the addition of 5 ppm 1-methyl-1-oxo-phospholine. After 2 liters of $CO_2$ have been generated, further carbodiimidization was interrupted by the addition of approximately 50 ppm zinc chloride. 994 g partially carbodiimidized 4,4'-diisocyanatodiphenylmethane was obtained having an NCO-content of 32% and a viscosity $\eta_{25°C}$ of 13 cP.

EXAMPLE 13

250 g of 4,4'-diisocyanatodiphenylmethane was melted and mixed with 0.4 ml of a 3% solution of 1-methoxy-1-oxo-phospholine in xylene. After 3 liters carbon dioxide had been generated, the catalyst was deactivated by the addition of 1 g 4,4'-biscarbamic acid bromide-diphenylmethane. 244 g partially carbodiimidized 4,4'-diisocyanatodiphenylmethane was obtained having an NCO-content of 27.8% and a viscosity of $\eta_{25°C}$ of 83 cP.

EXAMPLE 14

As described in Example 13, 250 g of 4,4'-diisocyanatodiphenylmethane was partially carbodiimidized but 1-butoxy-1-oxo-phospholine was used as the catalyst.

245 g of partially carbodiimidized 4,4'-diisocyanatodiphenylmethane was obtained having an NCO-content of 27.6% and a viscosity of $\eta_{25°C}$ of 96 cP.

EXAMPLE 15

290 g of 4,4'-diisocyanatodiphenylmethane was melted in a 500 ml reactor and mixed with 10 g of a tripropyleneglycol dropwise. Subsequently the mixture was stirred for 10 minutes and then mixed at 60° C with 0.2 ml of a 3% 1-ethyl-1-oxo-phospholine solution in tripropyleneglycol. A rapid carbodiimidization began which was detected through the carbon dioxide evolution. After 2 liters of $CO_2$ gas had evolved, the catalyst, was deactivated with 0.5 ml of butylcarbamic acid chloride.

925 g of a partially carbodiimidized mixture consisting of 4,4'-diisocyanatodiphenylmethane and a prepolymer of this compound with tripropyleneglycol was obtained $\eta_{25°C}$ 55 cP, NCO-content 28%.

EXAMPLE 16

266 g of o-tolylisocyanate (2 mol) was heated in a reactor to 160° C and after the addition of 1 ml of a 3% 1-methyl-1-oxo-phospholine solution in toluene was carbodiimized until 12 liters of carbon dioxide had evolved. Further $CO_2$ evolution was prevented by the addition of 0.5 ml phosphorus oxide chloride. The storage stable mixture having an NCO-content of 15.7% which was obtained, can be separated and purified by distillation. After fractionation and the separation of the non-carbodiimidized o-tolylisocyanate 110 g of o,o'-ditolylcarbodiimide were obtained having a boiling point of 131° to 133° C at 0.6 Torr. The o,o'-ditolylcarbodiimide obtained no phospholine oxide.

EXAMPLE 17

(Example of use)

200 parts by weight of a linear adipic acid ethyleneglycol-polyester of an OH-number 56 were dehydrated for 0.5 hours at 120° C in a water jet vacuum and subsequently heated with 70.5 parts, by weight, of the partially carbodiimidized 4,4'-diisocyanatodiphenylmethane of example 1 for 30 minutes to 120° to 125° C. 14 g butanediol-1,4 were added, mixed well, poured into a mold and reheated for 8 hours at 100° C. After 15 minutes the casting can be removed from the mold. It was characterized by extremely good mechanical values.

What is claimed is:

1. A process for the partial carbodiimidization of mono-, di-, and/or polyisocyanates, comprising:
   (a) mixing organic mono-, di-, and/or polyisocyanates with 0.1 to 100 ppm of a phosphorus compound of the general formula:

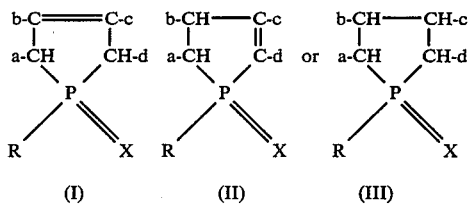

wherein R represents a lower alkyl radical, a phenyl radical, an alkoxy radical, a hydrogen atom or an alkenyl radical; a, b, c and d each represent hydrogen, a halogen atom, a lower alkyl, lower alkenyl, phenyl, a cyclohexyl or a polymethylene group which together with two neighboring C-atoms of the heterocyclic ring forms a cycloaliphatic ring; and X represents an oxygen or sulphur atom; at a temperature from about 0° to about 200° C, and,
   (b) terminating the carbodiimidization reaction after the evolution of 1 to 90% of the quantity of carbon dioxide to be theoretically expected in the carbodiimidization of all isocyanate groups present, by the addition of a quantity at least equivalent to the phosphorus compound used of a carbamic acid chloride or carbamic acid bromide which deactivates the catalyst while forming an adduct therewith.

2. A process according to claim 1, characterized in that compounds of the formula (I) or (II) are used as catalysts, and wherein R represents an unsubstituted alkyl radical having from 1 to 4 C-atoms, an unsubstituted alkoxy radical having from 1 to 4 carbon atoms or a phenyl radical, wherein, a, b, c and d which are identical or different radicals represent hydrogen or an unsubstituted alkyl radical having from 1 to 4 carbon atoms and X is oxygen.

3. The process of claim 1, wherein said temperature is from about 50° to about 150° C.

4. The process of claim 3, wherein said temperature is from about 90° to about 110° C, and wherein from about 1 to about 60 ppm of phosphorus compounds are used.

5. An isocyanate mixture having carbodiimide groups, characterized by a content of 0.1 to 100 ppm of phosphorus compounds of the formula:

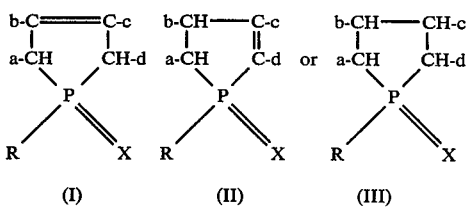

in deactivated form in respect of their catalytic effect by adduct formation with a carbamic acid chloride or a carbamic acid bromide wherein R represents a lower alkyl radical, a phenyl radical, an alkoxy radical, a hydrogen atom or an alkenyl radical; a, b, c and d each represent hydrogen, a halogen atom, a lower alkyl, lower alkenyl, phenyl, cyclohexyl or a polymethylene group which together with two neighboring C-atoms of the heterocyclic ring forms a cycloaliphatic ring; and X represents an oxygen or sulphur atom.

6. In an isocyanate polyaddition process, wherein an organic isocyanate is reacted with an active hydrogen containing material, the improvement wherein the isocyanate is an isocyanate mixture having carbodiimide groups, characterized by a content of 0.1 to 100 ppm of phosphorus compounds of the formula

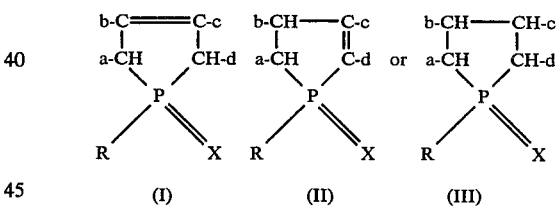

in deactivated form in respect of their catalyst effect by adduct formation with a carbamic acid chloride or a carbamic acid bromide wherein R represents a lower alkyl radical, phenyl radical, an alkoxy radical, a hydrogen atom or an alkenyl radical; a, b, c and d each represent hydrogen, a halogen atom, a lower alkyl, lower alkenyl, phenyl, a cyclohexyl or a polymethylene group which together with two neighboring C-atoms of the heterocyclic ring forms a cycloaliphatic ring; and X represents an oxygen or sulphur atom.

* * * * *